United States Patent [19]
Leonard

[11] Patent Number: 5,382,407
[45] Date of Patent: Jan. 17, 1995

[54] MEMBRANE BLOOD OXYGENATOR

[75] Inventor: Ronald J. Leonard, Ann Arbor, Mich.

[73] Assignee: Minnesota Mining and Manufacturing Company, St. Paul, Minn.

[21] Appl. No.: 957,415

[22] Filed: Oct. 5, 1992

Related U.S. Application Data

[63] Continuation-in-part of Ser. No. 657,338, Feb. 15, 1991, Pat. No. 5,152,964, which is a continuation of Ser. No. 248,092, Dec. 14, 1988, abandoned.

[51] Int. Cl.⁶ .............................................. A61M 1/14
[52] U.S. Cl. .............................. 422/48; 422/45; 422/46
[58] Field of Search ........................... 422/45, 46, 48

[56] References Cited

U.S. PATENT DOCUMENTS

| | | | |
|---|---|---|---|
| 3,526,481 | 9/1970 | Rubricius et al. | 23/256.5 |
| 3,717,174 | 2/1973 | Dewall | 137/565 |
| 3,794,468 | 2/1974 | Leonard | 23/258.5 |
| 3,927,980 | 12/1975 | Leonard | 23/258.5 |
| 4,466,804 | 8/1984 | Hino | 422/45 |
| 4,572,446 | 2/1986 | Leonard et al. | 242/7.02 |
| 4,690,758 | 9/1987 | Leonard et al. | 210/247 |
| 4,735,775 | 4/1988 | Leonard et al. | 422/46 |
| 4,767,289 | 8/1988 | Parrott et al. | 417/477 |
| 5,120,502 | 6/1992 | Gordon et al. | 422/46 |
| 5,152,964 | 10/1992 | Leonard | 422/48 |

FOREIGN PATENT DOCUMENTS

0373847  6/1990  European Pat. Off. .

Primary Examiner—Donald E. Czaja
Assistant Examiner—Lien Tran
Attorney, Agent, or Firm—Gary L. Griswold; Walter N. Kirn; Jeffrey J. Hohenshell

[57] ABSTRACT

A membrane oxygenator is disclosed. The oxygenator has a housing, gas and blood inlets and outlets, and a transfer membrane mechanism for transferring oxygen to blood. The oxygenator has a device for increasing its efficiency. The device maintains the total pressure of the oxygenating gas at each point within gas flow paths near yet below the total pressure of the blood opposite the transfer membrane mechanism generally throughout the oxygenator. The mechanism restricts the flow of oxygenating gas exiting through a oxygenating gas outlet with approximately the pressure of blood exiting through a blood outlet by providing a pressurization fluid with approximately the pressure of the blood exiting through the blood outlet. In a preferred embodiment, the oxygenating gas outlet is situated within the hollow portion of the housing.

11 Claims, 5 Drawing Sheets

MEMBRANE BLOOD OXYGENATOR

CROSS REFERENCE TO RELATED APPLICATIONS

This application is a continuation-in-part of U.S. Ser. No. 07/657,338 filed Feb. 15, 1991, now U.S. Pat. No. 5,152,964 issued Oct. 6, 1992, which was a continuation of U.S. Ser. No. 07/284,092 filed Dec. 14, 1988 now abandoned.

FIELD OF THE INVENTION

This invention relates to extracorporeal life support systems and particularly to extracorporeal membrane blood oxygenators for oxygenating a patient's venous blood prior to returning this blood to a patient's arterial system.

BACKGROUND ART

Extracorporeal blood oxygenators are widely used to add oxygen to and remove carbon dioxide from a patient's blood during those times when the patient's lungs do not satisfactorily perform this gas exchange function. One example of such a time is during coronary artery bypass graft surgery when the cardiac activity is electively stopped to facilitate the surgery. To perform this function for the lungs, the venous blood is drained from the heart into an extracorporeal oxygenator, oxygenated and returned to the aorta for recirculation throughout the patient's body.

Several types of oxygenators are available. Among these is the membrane oxygenator. A membrane oxygenator, in its basic form, comprises first and second conduits separated by a transfer membrane which is permeable to oxygen and carbon dioxide. During use of the membrane oxygenator, an oxygenating gas is caused to pass through one of the conduits while the patient's blood is caused to flow through the other conduit. Oxygen passes from the oxygenating gas through the transfer membrane and into the blood. Simultaneously, carbon dioxide passes from the blood through the transfer membrane and into the oxygenating gas.

The membrane oxygenator affords communication between the blood and the gas while preventing the actual mixing of the blood and the gas. For example, with a microporous hollow fiber membrane oxygenator, small pores in the walls of the fibers and the highly non-wetting nature of the wall material afford the communication between the blood and the oxygenating gas.

One known way to improve the performance of these membrane oxygenators is to simply provide more membrane surface area. Another known way to improve the performance of membrane oxygenators is to increase the amount of gas transfer per unit of transfer membrane surface area by improving blood mixing over the membrane surface. Some of the highest gas transfer rates for membrane blood oxygenators are believed to be associated with hollow fiber membrane oxygenators as described, for example, in U.S. Pat. Nos. 4,690,758 and 4,735,775. In these oxygenators, the oxygenating gas flows through the hollow fibers and the patient's blood flows around the hollow fibers.

Another known way to improve the performance of membrane oxygenators is to vary the partial pressure difference of the diffusing oxygen and carbon dioxide on opposite sides of the membrane. However, a limiting factor at least with respect to microporous hollow fiber membrane oxygenators is the need to maintain the total pressure of the oxygenating gas at each place within the oxygenator generally at or below the total pressure of the blood opposite the membrane within the oxygenator to avoid bubbling the oxygenating gas into the blood with the attendant risks associated with a gas embolism. Avoidance of the formation of gas bubbles within the blood is complicated by, among other things, the variance of the blood pressure and the variance of the gas pressure within the oxygenator. These pressures are reflective of the differing oxygen and carbon dioxide needs of different patients and the differing needs of a single patient over time. Efforts in the past to maintain the total pressure of the oxygenating gas below that of the blood across the membrane have included simply venting the outlet of the oxygenating gas to atmosphere through a relatively low pressure drop gas path.

SUMMARY OF THE INVENTION

The present invention provides a membrane blood oxygenator having means for automatically maintaining the total pressure of the oxygenating gas near yet below that of the blood across the membrane. In one embodiment, the oxygenator comprises a housing having a hollow portion receiving a hollow fiber bundle defining oxygenating gas flow paths inside the fibers and means for automatically maintaining the total pressure of the oxygenating gas at each place within the bundle near yet below the total pressure of the blood opposite the bundle generally throughout the bundle. The automatically maintaining means comprises means for restricting the flow of oxygenating gas exiting the oxygenator with the pressure of the blood exiting the oxygenator and preferably includes a valve member and tubing communicating the pressure of the exiting blood to the valve member to activate the valve member.

In another embodiment of the present invention, the oxygenator comprises a housing having a hollow portion, and transfer membrane means comprising a hollow fiber bundle disposed within the hollow portion of the housing. The transfer membrane means define oxygenating gas flow paths between an oxygenating gas inlet and an oxygenating gas outlet and through individual fibers in the hollow fiber bundle, and define blood flow paths between a blood inlet and a blood outlet and around individual fibers in the hollow fiber bundle. A means for maintaining the total pressure of the oxygenating gas at each point within the gas flow paths near yet below the total pressure of the blood opposite the transfer membrane means generally throughout the oxygenator is also present. The maintaining means comprises means for restricting the flow of oxygenating gas exiting through the oxygenating gas outlet by providing a pressurization fluid with approximately the pressure of the blood in the blood flow paths to raise the pressure of the oxygenating gas within the oxygenator to increase the efficiency of the oxygenator.

With respect to the second embodiment, preferably, the pressurization fluid is situated in the hollow portion of the housing and comprises blood. Also preferably, the oxygenating gas outlet is situated within the hollow portion of the housing.

Also, in the second embodiment, the automatic maintaining means preferably comprises a tube situated within the hollow portion of the housing and having an inlet connected to the oxygenating gas outlet and an oxygenator outlet for passage of the oxygenating gas out of the oxygenator. The tube has a flexible resilient portion adapted to be partially collapsed by the pressurization fluid and a relatively rigid portion for resisting collapse due to the pressurization fluid. Preferably, the flexible, resilient portion is situated generally adjacent the blood outlet.

BRIEF DESCRIPTION OF THE DRAWING

The invention is illustrated in the accompanying drawing wherein like numbers refer to like parts.

FIGS. 9 through 11 are schematic views which sequentially illustrate the collapse of a first flexible, resilient element for use with the embodiment shown in FIG. 8 wherein:

FIGS. 12 and 13 sequentially illustrate a second flexible, resilient element for use with the embodiment shown in FIG. 8 wherein:

FIGS. 14 and 15 sequentially illustrate a third flexible, resilient element for use with the embodiment shown in FIG. 8 wherein:

DETAILED DESCRIPTION

Figure 1:
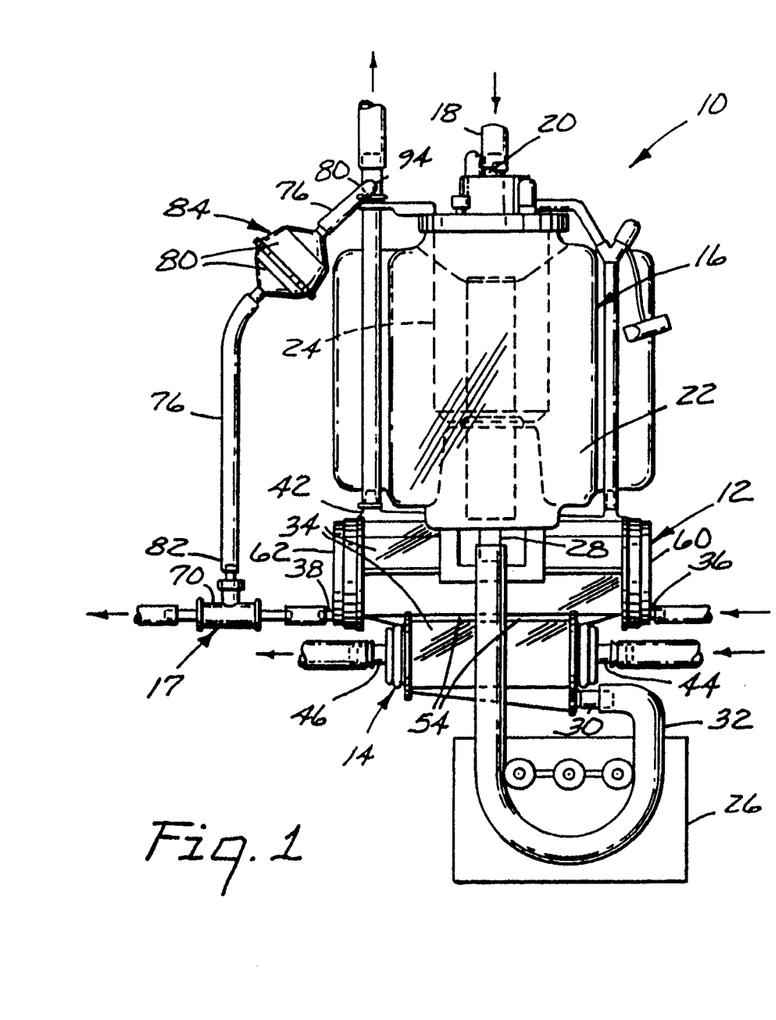
FIG. 1 is a front elevational view of the extracorporeal device of a first embodiment of the present invention.
Figure 2:
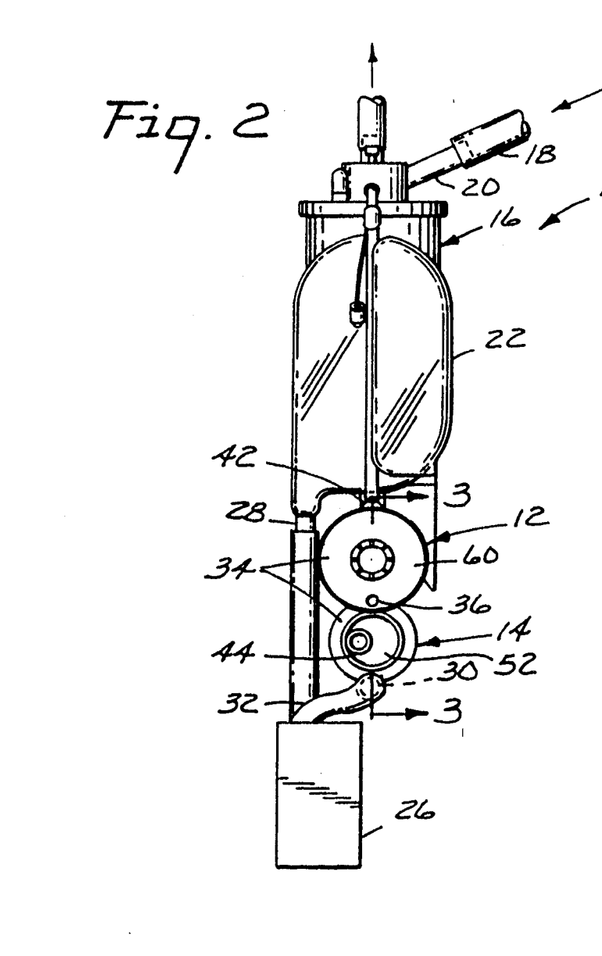
FIG. 2 is a side elevational view of the device of FIG. 1.

Referring now to FIGS. 1 through 7 of the drawing, there is shown in FIGS. 1 and 2 an extracorporeal device 10 of the first embodiment of the present invention generally comprising a hollow fiber membrane oxygenator 12, a heat exchanger 14, a venous reservoir 16, and a valve 17 for pressurizing the oxygenating gas. The device 10 mounts on a Sarns Oxygenator Unit Bracket, part number 164490, available from Sarns Inc., Ann Arbor, Mich., U.S.A. The device 10 is used with a Sarns Oxygen-Air Blender, part number 164235, also available from Sarns Inc. The venous reservoir 16 debubbles, filters and stores venous blood prior to oxygenation. The oxygenator 12 adds oxygen to and removes carbon dioxide from the blood. The heat exchanger 14 heats or cools blood. A suitable combination reservoir, oxygenator and heat exchanger is available from Sarns Inc. as part number 16385.

The venous blood is drained from a patient in conventional fashion and delivered to the device 10 through medical-grade tubing 18. The tubing 18 is suitably attached to a conventional blood inlet 20 in fluid communication with the venous reservoir 16 so that the venous blood can pass into the body 22 via the blood defoamer and/or filter 24.

When a conventional blood pump 26 is activated, the blood is drawn from an outlet 28 of the reservoir 16 and delivered to an inlet 30 of the heat exchanger 14 through medical-grade tubing 32. Suitable blood pumps are available from Sarns Inc. In the embodiment, the heat exchanger 14 and the oxygenator 12 are disposed in a housing 34. This housing 34 includes a first fluid inlet 36 which is used as an oxygenating gas inlet, a first fluid outlet 38 which is used as an oxygenating gas outlet, a second fluid inlet 30 which is used as a blood inlet, a second fluid outlet 42 which is used as a blood outlet, a third fluid inlet 44 which is used as a heat transfer fluid inlet, and a third fluid outlet 46 which is used as a heat transfer fluid outlet.

Figure 3:
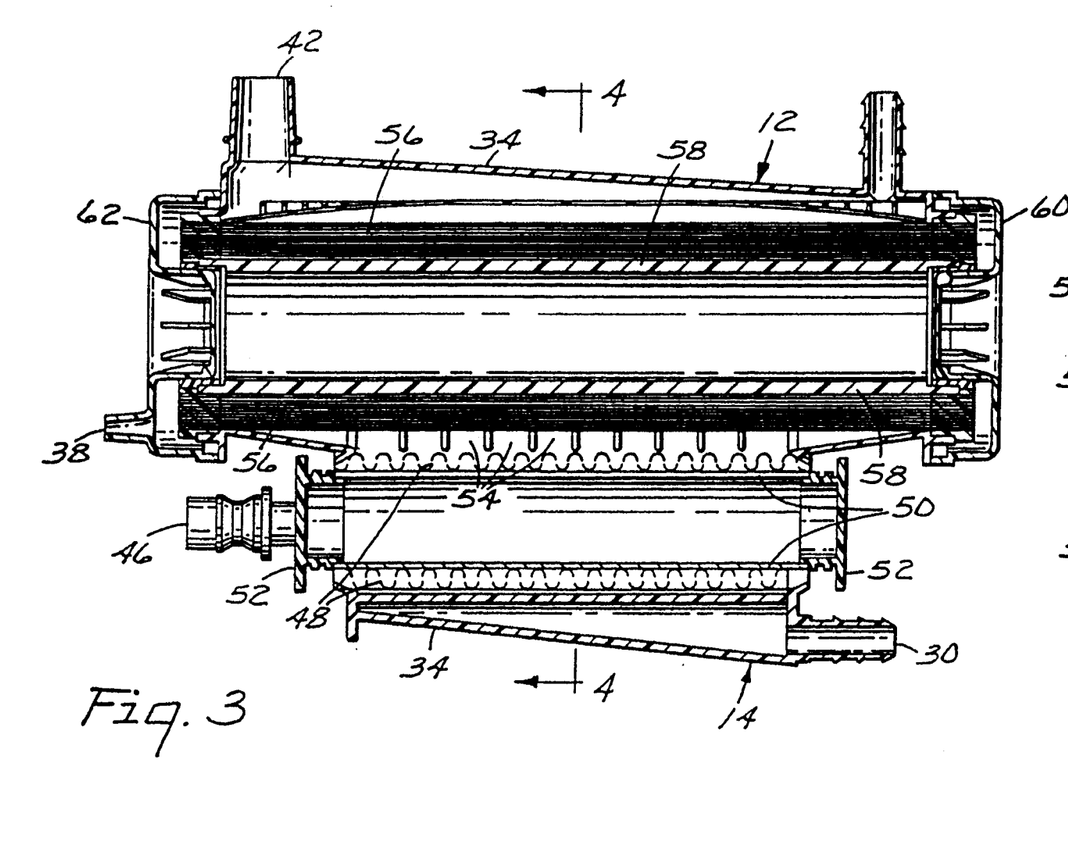
FIG. 3 is an enlarged sectional view taken approximately along the line 3—3 of FIG. 2.
Figure 4:
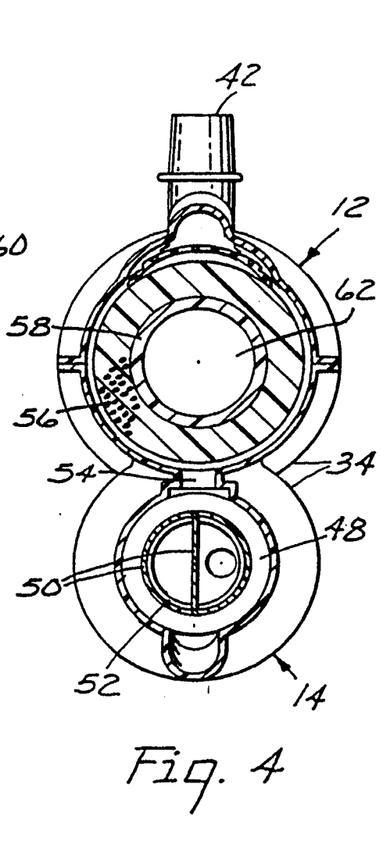
FIG. 4 is a sectional view taken approximately along the line 4—4 of FIG. 3.

Referring to FIGS. 3 and 4, the heat exchanger 14 includes a core 48, a manifold 50, end caps 52, inlet 44 and outlet 46. A passageway 54 couples the heat exchanger 14 with the outside of a microporous, hollow fiber bundle 56 within the oxygenator 12. The bundle 56 is wound about a plastic core 58 as is well known in the art. See, for example, U.S. Pat. Nos. 4,735,775, 4,690,758, 4,572,446 and 3,794,468. The hollow fiber bundle 56 is encapsulated at its ends by means of a potting compound, although the ends of the hollow fibers are open to form oxygenating gas flow paths as is known in the art. End caps 60 and 62 secure the ends of the oxygenator 12.

The blood path is into the second inlet 30, around the outside of the heat exchanger core 48 where the blood is heated or cooled, as the case may be, along the passageway 54 to the oxygenator 12, around the individual fibers of bundle 56 where the blood is enriched with oxygen and finally out of the second outlet 42. The heat transfer fluid, typically water, follows a path via the third inlet 44, through the heat exchanger manifold 50 and core 48 and out the third outlet 46. The oxygenating gas path is into the first inlet 36, through the individual fibers of bundle 56 and out the first outlet 38. The first, second and third inlets and outlets are of conventional design so that the oxygenating gas and water can be supplied from conventional sources.

Figures 5, 6, 7:
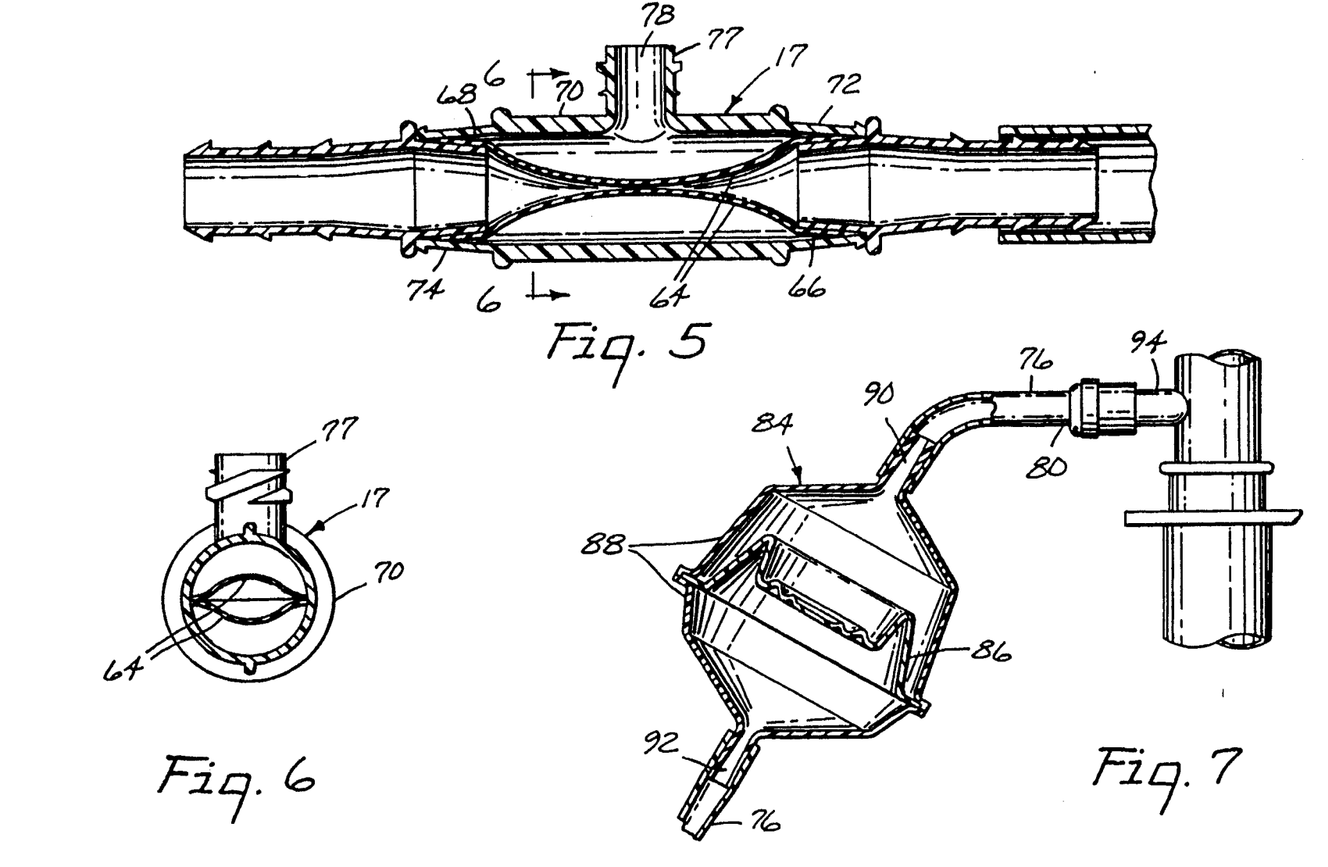
FIG. 5 is an enlarged vertical sectional view of a valve member of the device of FIG. 1 that can restrict the flow of oxygenating gas exiting the device of FIG. 1.
FIG. 6 is a sectional view taken approximately along the line 6—6 of FIG. 5.
FIG. 7 is an enlarged elevational view of a fluid transducer of the device of FIG. 1 that can communicate the pressure of blood exiting the device of FIG. 1 to the valve member of FIGS. 1, 5 and 6 to restrict the flow of oxygenating gas exiting the device of FIG. 1.

Referring now to FIGS. 1, 2, 5, 6 and 7 and in particular to FIG. 5, there is shown the valve 17 for pressurizing the oxygenating gas. The valve 17 includes an inner tube 64 having an inlet 66 and an outlet 68, a housing 70, an inlet portion 72, an outlet portion 74 and means for maintaining an above-ambient pressure in the area between the housing 70 and the inner tube 64. The inner tube 64 is received within the housing 70. The inlet portion 72 connects the housing 70 to the inner tube 64 adjacent the inlet 66 of the inner tube 64. The outlet portion 74 connects the housing 70 to the inner tube 64 adjacent the outlet 68 of the inner tube 64. The inner tube 64 is preferably relatively soft and flexible and comprised of a thin walled vinyl, urethane or silicone rubber material conventionally heat sealed along two longitudinally aligned, parallel edges and having a wall thickness in the range of about 0.001–0.020 inches. The inner tube 64 preferably is sufficiently soft and flexible to offer little or no resistance to externally applied pressures; i.e., the inner tube 64 freely opens and closes in cross section in response to pressure differences between the inside and the outside of the tube 64. The housing 70 is preferably comprised of a relatively rigid polycarbonate or acrylic plastic material.

The means for maintaining the above-ambient pressure in the area between the housing 70 and the inner tube 64 includes a tubing 76 communicating the pressure of the blood exiting the oxygenator 12 to the area between the housing 70 and the inner tube 64. The housing 70 has a portion 77 having an aperture 78 there through. The tubing 76 has an inlet 80 in fluid communication with the second outlet 42 of the housing 34 and the tubing 76 has an outlet 82 in fluid communication with the aperture 78 through the housing 70 of the valve 17 so that the pressure in the area between the housing 70 and the inner tube 64 approaches that of the exiting blood at the inlet 80 of the tubing 76. Preferably, the blood does not directly occupy the area between the housing 70 and the inner tube 64. This avoids possible over-pressurization of the valve 17 by a column of blood in the tubing 76. Instead, a fluid transducer 84 communicates the exiting blood pressure to the area between the housing 70 and the inner tube 64 via a diaphragm 86.

Referring specifically to FIG. 7, the transducer 84 generally comprises a two-piece housing 88 enclosing and supporting the diaphragm 86. A suitable transducer is a pressure isolator available from Gish Biomedical, Inc., Santa Ana, Calif., U.S.A. The transducer 84 includes an inlet 90 in fluid communication with the inlet 80 of the tubing 76 and an outlet 92 in fluid communication with the outlet 82 of the tubing 76. The portion of the tubing 76 between the transducer 84 and the valve 17 can be filled with air or another suitable fluid. The tubing 76 is connected to a fluid access port 94 at a vertical distance with respect to gravity from the second outlet 42 of the housing 34 of the oxygenator 12.

The operation of the extracorporeal device 10 will next be described with reference generally to the figures of the drawing. As noted earlier, the device 10 is preferably connected to the oxygen-air blender in conventional fashion at the first inlet 36. Similarly, the device 10 is preferably connected to a conventional source of heated or cooled water at the third inlet 44. After these connections have been made and adjusted to the user's satisfaction, the pump 26 is activated, and blood is drawn from the body 22 of the reservoir 16 and delivered to the second inlet 30. From the second inlet 30, the blood is pumped through the heat exchanger 14 where it is suitably heated or cooled, passed through the passageway 54, and on to and through the oxygenator 12 where oxygen/carbon dioxide exchange takes place. Finally, the blood is pumped out the second outlet 42 and past the fluid access port 94.

The fluid access port 94 is preferably disposed a predetermined vertical distance with respect to gravity from the outlet 42 sufficient to ensure that the blood pressure at the inlet 80 will be near yet below the blood pressure of the blood at each place within the oxygenator 12. The blood pressure at the inlet 80 of the tubing 76 is preferably in the range of about 0–500 mmHg above ambient atmospheric and most preferably is about 300 mmHg.

The blood pressure at the inlet 80 of the tubing 76 is communicated to the blood side of the diaphragm 86 of the fluid transducer 84 through the inlet 90 of the transducer 84. This pressure deforms or otherwise moves the diaphragm 86 to pressurize a suitable fluid in the lower portion of the tube 76, which in turn communicates this pressure to the valve 17. Assuming a negligible head height difference between the inlet 80 and the transducer 84 and the usage of a suitably light fluid such as air in the lower portion of the tubing 76, the pressure communicated to the valve 17 will closely approximate that present at the inlet 80.

The pressure communicated to the valve 17 is communicated to the area between the housing 70 and the inner tube 64 through the aperture 78. As noted earlier, this pressure is most preferably about 300 mmHg. This pressure tends to urge the inner tube 64 to close against the pressure of the oxygenating gas exiting the first outlet 38 of the device 10. This urging, in turn, raises the pressure of the oxygenating gas exiting the first outlet 38 to approximately that of the blood at the fluid access port 94, assuming a negligible pressure drop across the valve 17. Assuming a negligible pressure drop across the oxygenator 12, this raises the pressure of oxygenating gas within the oxygenator 12 to near yet below the blood pressure at the fluid access port 94, which is near yet below the total blood pressure opposite the bundle 56 of the oxygenator 12 generally throughout the bundle 56. Whatever pressure drops that do exist between the fluid access port 94 and the bundle 56 through the route of the tubing 76 will only greater ensure that the pressure of the oxygenator gas at each place within the bundle 56 is below the total pressure of the blood opposite the bundle 56 generally throughout the bundle 56.

The pressure of the oxygenating gas is self-regulating to stay near yet below the blood pressure due to the construction, location and operation of the tubing 76 together with the transducer 84 and the valve 17. In operation, there is a positive pressure at access port 94 due to the blood flow provided by pump 26 and the resistance of the rest of the system. Typically this pressure may range from 100 to 500 mmHg above ambient depending upon the selection and size the individual items of the extracorporeal life support system, the vascular state of the patient, and the blood flow rate. It is known that the transfer rate of a gas into a liquid such as blood is a function of the partial pressure driving force between the gas and the liquid and not the liquid pressure itself. Hence, as the blood flow increases, normally indicating increased patient oxygen demand, the oxygen transfer will be automatically increased as the higher flow is reflected as a higher pressure to the gas path by means of the tubing 76, transducer 84 and valve 17. As the blood flow decreases, the opposite happens.

Carbon dioxide transfer may actually be impaired by the action of this invention, since the partial pressure of the carbon dioxide in the gas path will also be increased by the action of increasing the gas path pressure. However, membrane oxygenators employing microporous membranes generally have carbon dioxide transfer rates at high gas flows which are substantially higher than their oxygen transfer capabilities. In that sense the device 10 of the present invention actually helps in that it tends to moderate the imbalance in transfer rates. Additionally, patients normally produce carbon dioxide at a rate lower than their oxygen consumption as reflected in the respiratory quotient. This is the ratio of carbon dioxide production to oxygen consumption and is generally on the order of about 0.8.

The action of the device 10 of this invention can be moderated in several ways. The percent oxygen in the oxygenating gas can be used to trim the oxygen transfer rate as is now done with standard oxygenators. The arterial line might actually be restricted using a Harvard clamp or the like to increase the arterial line pressure and thereby further increase the performance of the oxygenator. This could be done on a temporary basis in case of some transient high oxygen demand from the patient. Also, valve 17 can be effectively eliminated by closing a valve (not shown) at the access port 94 and venting the pressure at outlet 38 to interrupt the action of the gas pressure control and return to normal atmospheric operation. This might be done during times of minimal oxygen demand such as at very low patient temperatures, where the patient metabolic rate is very low.

The operation of the above-described device 10 can perhaps be better understood with reference to the following examples. The first example uses the standard Sarns oxygenator, part number 16385 as identified earlier. This oxygenator exhibits a blood outlet oxygen partial pressure of approximately 80 mmHg when operated with a blood inlet oxygen partial pressure of 35 mmHg with normal standard blood at 6 liters per minute of blood flow. When the oxygenator is equipped with the tubing 76, transducer 84 and valve 17 of the device 10 of the present invention and is used at an arterial line blood pressure of about 300 mmHg, and therefore a similar increase in the gas pressure by way of the invention, the outlet oxygen partial pressure in the blood is 215 mmHg. This indicates that the device 10 of this invention improves the performance of a conventional hollow fiber membrane oxygenator.

For the second example, a second oxygenator was constructed similar to the standard Sarns oxygenator, but with a fiber area of only 1.0 square meters as opposed to 1.8 square meters for the standard device. Operated under the conditions of the first example, the blood outlet oxygen partial pressure was only about 66 mmHg without the addition of the tubing 76, transducer 84 and valve 17 as would be expected due to the reduced surface area for transfer. When the oxygenator was so equipped and used with a line pressure of 300 mmHg, the blood outlet oxygen partial pressure was about 100 mmHg. This indicates that the device 10 of this invention would allow a decrease in the surface area of the standard Sarns oxygenator by almost 50 percent, while retaining approximately the same level of performance. This would allow both cost reduction, reduction in the exposure of blood to foreign surfaces, and a reduction in priming volume. These are generally known to be important patient concerns.

Figure 8:
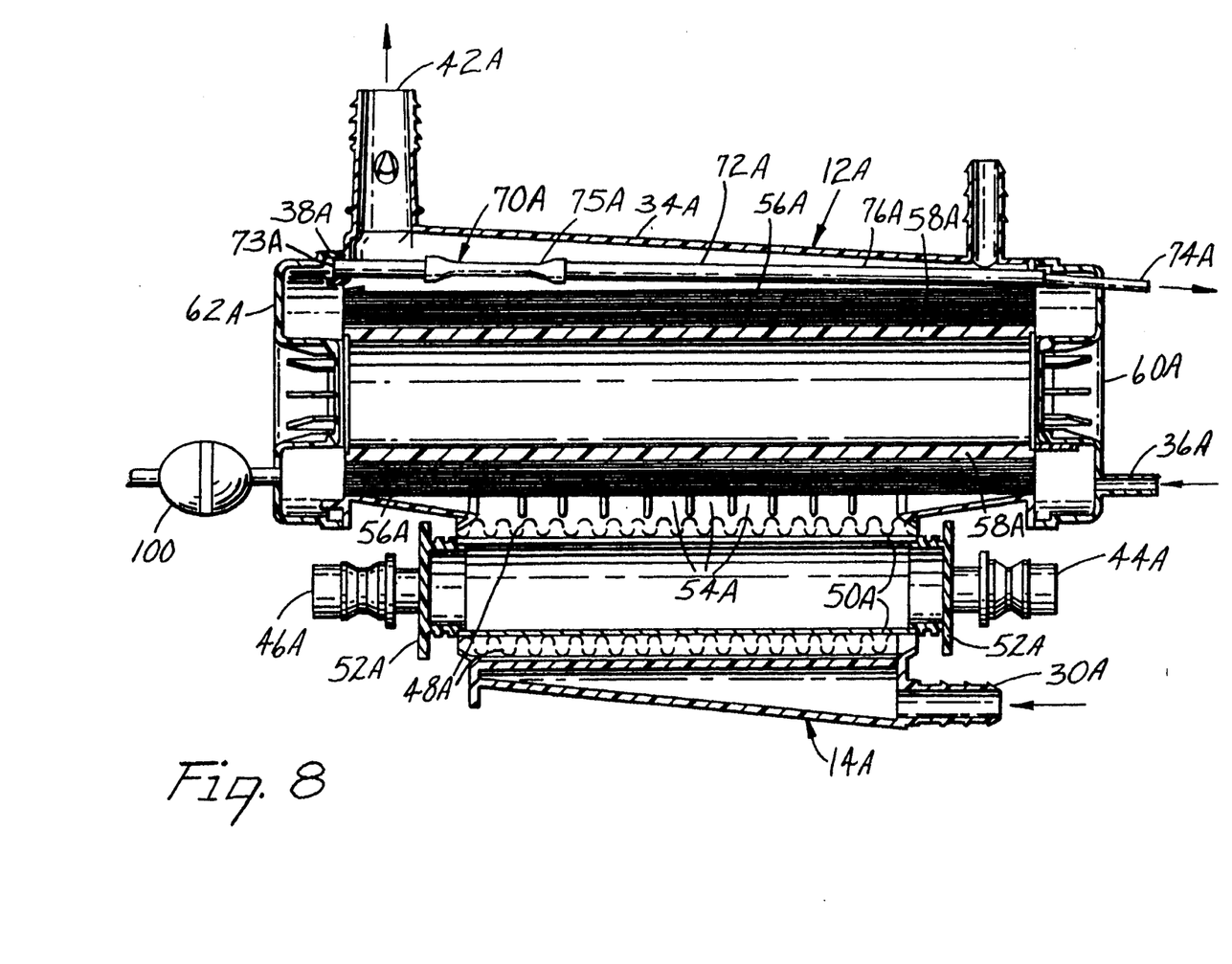
FIG. 8 is an enlarged, partial sectional view of a second embodiment of oxygenator similar to the section taken to provide FIG. 3, but showing a tube having flexible and rigid portions within the oxygenator housing.

Referring now to FIG. 8, there is shown a second embodiment of the present invention generally designated by reference character 12A. The second embodiment of oxygenator 12A affords lower cost, priming volumes, and less blood surface contact that may damage blood as compared to the oxygenator 12.

The membrane oxygenator 12A is an element in an excorporeal device which includes a heat exchanger 14A and a venous reservoir (not shown but similar to reservoir 16 described above). The device mounts on a Sarns Oxygenator Unit Bracket, part number 164490, available from Sarns Inc., Ann Arbor, Mich., U.S.A. The device is used with a Sarns Oxygen-Air Blender, part number 164235, also available from Sarns Inc. A suitable reservoir is available from Sarns Inc. as part number 98-0702-0518-6.

The venous blood is drained from a patient in conventional fashion and delivered to the device through medical-grade tubing. The tubing is suitably attached to a conventional blood inlet (not shown but similar to 20 described and shown above with reference to FIG. 1) in fluid communication with the venous reservoir so that the venous blood can pass into the body (e.g. 22) of the reservoir via the blood defoamer and/or filter (e.g. 24).

When a conventional blood pump (e.g. 26) is activated, the blood is drawn from an outlet (e.g. 28) of the reservoir and delivered to an inlet 30A of the heat exchanger 14A through medical-grade tubing. Suitable blood pumps are available from Sarns Inc. In this embodiment, the heat exchanger 14A and the oxygenator 12A are disposed in a housing 34A.

As the blood flows through the oxygenator, it naturally undergoes a pressure drop from blood inlet 30A to blood outlet 42A of perhaps as much as 100 mmHg. In addition due to the patient arterial pressure, the gravity head up to the operating table, the resistance of the arterial line, the resistance of the cannula into the patient, and the arterial bubble trap or filter there is a back pressure at the oxygenator blood outlet 42A. The back pressure will vary from as low as 50 mmHg to over 400 mmHg depending on the arrangement of the circuit, blood temperatures, blood hematocrit, and the flow rate of blood. Thus, pressure is available in the oxygenator 12A to be utilized according to the present invention.

The oxygenator 12A comprises a housing 34A having means defining a hollow portion, and transfer membrane means comprising a hollow fiber bundle 56A disposed within the hollow portion of the housing 34A. The transfer membrane means defines oxygenating gas flow paths between an oxygenating gas inlet 36A and an oxygenating gas outlet 38A and through individual fibers in the hollow fiber bundle 56A. The transfer membrane means also defines blood flow paths between a blood inlet 30A and a blood outlet 42A and around individual fibers in the hollow fiber bundle 56A.

The heat exchanger 14A has fluid inlet 44A which is used as a heat transfer fluid inlet, and a fluid outlet 46A which is used as a heat transfer fluid outlet. Like the heat exchanger 14, the heat exchanger 14A includes a core 48A, a manifold 50A, end caps 52A, inlet 44A and outlet 46A. A passageway 54A couples the heat exchanger 14A with the outside of a microporous, hollow fiber bundle 56A within the oxygenator 12A. The bundle 56A is wound about a plastic core 58A as is well known in the art. See, for example, U.S. Pat. Nos. 4,735,775, 4,690,758, 4,572,446 and 3,794,468, the entire contents of which are herein expressly incorporated by reference.

The hollow fiber bundle 56A is encapsulated at its ends by means of a potting or "sealing" compound, although the ends of the hollow fibers are open to form oxygenating gas flow paths. For example, a two part urethane polymer system, generally available from Anderson Chemical Co. of Anderson, Ind. or the like may be used. End caps 60A and 62A secure the ends of the oxygenator 12A.

The blood path is into the blood inlet 30A, around the outside of the heat exchanger core 48A where the blood is heated or cooled, as the case may be, along the passageway 54A to the oxygenator 12A, around the individual fibers of bundle 56A where the blood is enriched with oxygen and finally out of the blood outlet 42A. The heat transfer fluid, typically water, follows a path via the inlet 44A, through the heat exchanger manifold 50A and core 48A and out the outlet 46A.

Unlike the oxygenator 12, the oxygenator 12A has a slightly different oxygenating gas path. The oxygenating gas path is into the inlet 36A, into a sealed, hollow chamber in cap 60A, through the individual fibers of bundle 56A, into a sealed, hollow chamber within cap 62A, out the first outlet 38A, then through a tube 72A, and finally out outlet 74A. It should be noted that incoming gas in the hollow portion of gas cap 60A does not mix with exiting gas that flows through outlet 74A.

The oxygenating gas undergoes a pressure drop as it passes through the fiber bores in the bundle 56A, but due to the low viscosity of gas and the numerous openings for flow, the pressure drop in low. A typical value of pressure drop is believed to be about 5 mmHg. Thus, the pressure of the oxygenating gas in the oxygenator 12A is not unduly affected by the pressure drop due to the fiber bores in the bundle 56A.

Normally a valve 100 in cap 62A is closed so that the oxygenating gas flows through the lumen of tube 72A and out of the oxygenator 12A through oxygenator gas outlet 74A. However, optionally the valve 100 may be opened. For example, if the patient were small and easily oxygenated, the valve 100 might be opened to allow easier control of oxygen partial pressure without the added controlling effect of the blood pressure. Additionally, the valve 100 may also be opened during times of minimal oxygen demand such as at very low patient temperatures, where the patient metabolic rate is very low.

The valve 100 provides an immediate way of controlling the effect of a means 70A (described below) in a direct acting manner. Optionally, but not preferably, the means 70A could be used only for large patients or when blood gas values were low for other reasons. This allows one oxygenator 12A to serve a very wide patient size population.

The means 70A automatically maintains the total pressure of the oxygenating gas at each point within the gas flow paths near yet below the total pressure of the blood opposite the transfer membrane means 56A generally throughout the oxygenator 12A. The automatic maintaining means 70A comprises means for restricting the flow of oxygenating gas exiting through the oxygenating gas outlet 38A by providing a pressurization fluid with approximately the pressure of the blood in the blood flow paths to raise the pressure of the oxygenating gas within the oxygenator to increase the efficiency of the oxygenator 12A.

The means 70A automatically raises the pressure of the oxygenating gas within the oxygenator as opposed to, for example, devices which include electronic sensors or electronic control circuitry which introduce the possibility of electronic failure and undesirable electronic response times into the device.

FIG. 8 illustrates a preferred example of the means 70A. The means 70A includes situating the oxygenating gas outlet 38A within the hollow portion of the housing 34A. The means 70A also comprises the tube 72A situated within the hollow portion of the housing 34A and having an inlet 73A connected to the oxygenating gas outlet 38A and an oxygenator outlet 74A for passage of the oxygenating gas out of the oxygenator 12A. The tube 72A has a flexible resilient portion 75A adapted to be partially collapsed by the pressurization fluid and a relatively rigid portion 76A for resisting collapse due to the pressurization fluid.

Preferably, the pressurization fluid is situated in the hollow portion of the housing 34A and comprises blood. More preferably, the flexible, resilient portion 75A is situated generally adjacent the blood outlet 42A so that the pressure of the pressurization fluid is approximately the pressure of the blood exiting the oxygenator through blood outlet 42A. Locating the tube 72A within the hollow portion of housing 34A allows it to respond quickly to pressure changes. This technique limits the number of connections and eliminates duplicate operating chambers. The position also protects the tube 72A from line kinks or accidental occlusions that might jeopardize the increased efficiency effect of the means 70A or create unsafe operation.

Since the gas pressure will always be lower than the blood pressure, leakage of the means 70A however remote leads to blood leaking into the tube with minor consequences compared to gas entering the blood path. Failure of the means 70A is believed to be similar to the failure of a fiber in the bundle 56A.

Optionally, the flexible resilient portion 75A does not completely restrict flow of the oxygenating gas through oxygenator outlet 74A. The collapsing resilient portion 75A is selected so that, in the fully collapsed state, it nevertheless allows enough oxygenating gas flow to limit the gas path pressure effect of the means 70A to a predetermined value (such as 300 mmHg), even though the blood pressure increases beyond the predetermined value.

Figure 9:
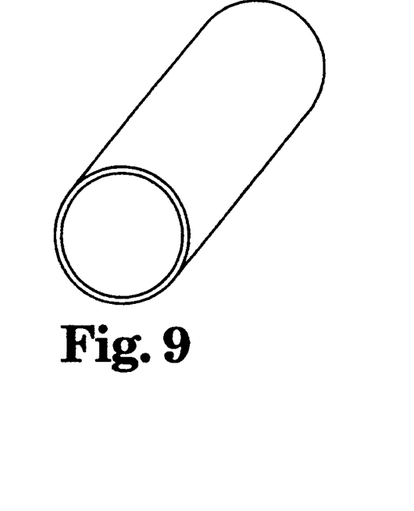
FIG. 9 is a perspective view of the resilient element just before pressure such as blood pressure is applied to its outer surfaces.
Figure 10:
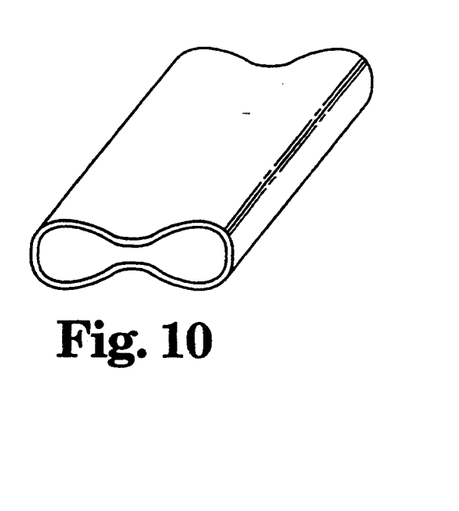
FIG. 10 is a perspective view of the resilient element of FIG. 9 just after pressure is applied showing the deformation of the element.
Figures 11, 12, 13, 14, 15:
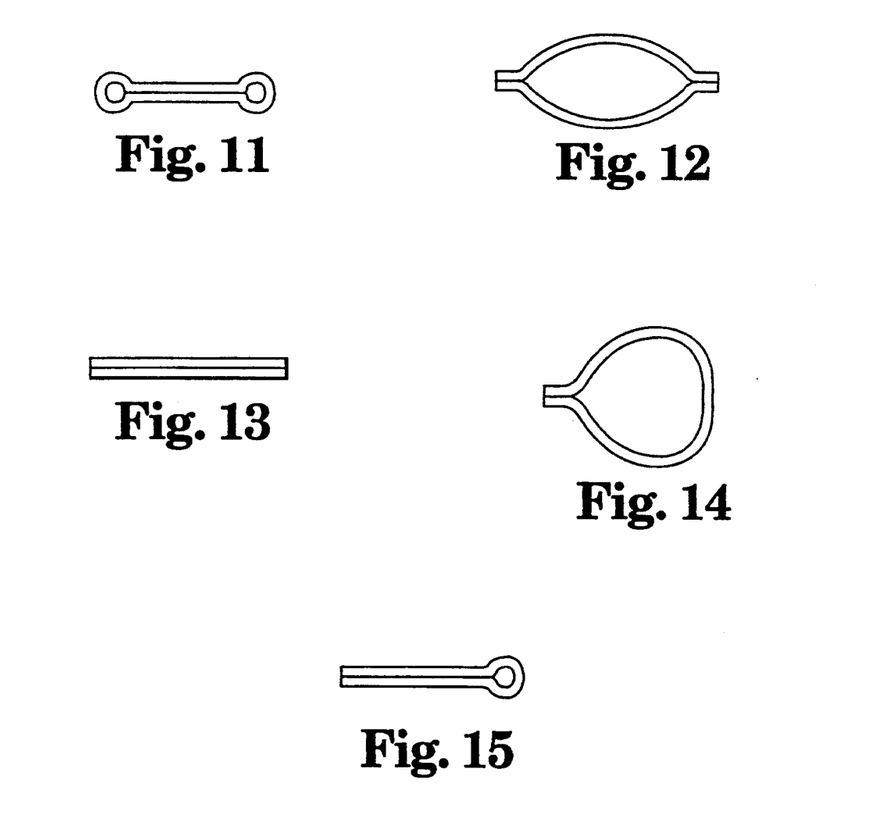
FIG. 11 is a sectional view of the resilient element of FIG. 9 after the element has been almost completely collapsed.
FIG. 12 is a sectional, schematic view showing heat sealed sides of the flexible resilient element just before pressure is applied to its outer surfaces.
FIG. 13 is a sectional, schematic view of the element of FIG. 12 showing it completely collapsed due to pressure at its outer surfaces.
FIG. 14 is a sectional view showing an element with one heat sealed side just before pressure is applied to its outer surfaces.
FIG. 15 is a section view of the element of FIG. 14 after the element is almost completely collapsed.

FIGS. 9 through 11 sequentially illustrate the collapse of a first embodiment of a flexible, resilient portion 75A for use with the embodiment shown in FIG. 8. The round tube is shown in FIG. 9 just before pressure such as blood pressure is applied to its outer surfaces. The tube begins to assume approximately an elliptical shape initially after pressure is applied. Note FIG. 10. As the external (e.g. blood) pressure increases relative to the internal (oxygenating gas) pressure, the tube assumes the shape shown in FIG. 11. As shown in FIG. 11, the walls of the center portion of the tube are in contact, but due to the small diameter assumed by the edges as the tube collapses, there is a slight passage near the tube's edge. The final diameter of these passages is believed to be a function of the tube diameter, the wall thickness, the wall material, and the applied pressure.

The rate of reduction in the diameter of the passages at the edges diminishes (for a given increment of applied external pressure) as the diameter of the passage itself diminishes. Thus, the tube resists complete collapse. The passages afford oxygenating gas flow even though the main body of the tube is collapsed. Since this small passage exists, the pressure created in the oxygenating gas flow due to the external blood pressure will be less than the blood pressure, since the flow of oxygenating gas is not totally controlled by the external pressure.

The embodiment of the flexible portion 75A shown in FIGS. 9-11 may be used to retain the oxygenating gas pressure in the tube less than the applied (blood) pressure or even to essentially control the upper limit gas pressure in the tube for a given gas flow rate.

FIGS. 12 and 13 sequentially illustrate a second embodiment of a flexible, resilient portion 75A for use with the embodiment of oxygenator shown in FIG. 8. As shown in FIG. 12, the edges of the tube have been heat sealed flat. The tube now collapses completely since the heat sealing operation eliminates the possibility of a passage forming at the edges.

FIGS. 14 and 15 sequentially illustrate a third embodiment of a flexible, resilient portion for use with the oxygenator shown in FIG. 12A. The tube is sealed only on one edge so only one passage is formed at the non-sealed edge. An intermediate effect is obtained. Additionally, the tube might be heat sealed along only a portion of its edge to control the passage length, thus also controlling the flow through the resulting passage and thereby the pressure created in the tube.

Another alternative for constructing the tube 72A would be to insert a small, rigid tube (not shown) within the resilient portion 75A. The rigid tube resists deformation due to the blood pressure. Thus, the complete occlusion of the oxygenating gas flow may be avoided according to the present invention. However, many different methods of preventing a complete occlusion of oxygenating gas flow may be utilized, thus, the present invention should not be unduly limited to the above examples.

The tube 72A may be constructed from any suitable material which is inert to blood and otherwise suitable for this medical purpose. For example, the resilient portion 75A may be constructed from a thin walled urethane, silicone rubber or soft vinyl, and the more rigid portion 76A (and optionally the small tube) may be constructed from semi-rigid vinyl. The resilient portion 75A may be heat sealed to the more rigid portion 76A. Preferably, the resilient portion 75A has a wall thickness of between about 0.005 and about 0.020 inches, and a diameter of between about 0.3 centimeters and about 1 centimeter, and is preferably approximately 0.5 centimeters.

The operation of the extracorporeal device (similar to 10 in FIG. 1) and the oxygenator 12A will next be described with reference generally to FIG. 8 of the drawing. As noted earlier, the device is preferably connected to the oxygen-air blender in conventional fashion at the first inlet 36A. Similarly, the device is preferably connected to a conventional source of heated or cooled water at the third inlet 44A. After these connections have been made and adjusted to the user's satisfaction, the pump (e.g. 26) is activated, and blood is drawn from the body of the reservoir (e.g. 16) and delivered to the second inlet 30A. From the second inlet 30A, the blood is pumped through the heat exchanger 14A where it is suitably heated or cooled, passed through the passageway 54A, and on to and through the oxygenator 12A where oxygen/carbon dioxide exchange takes place. Finally, the blood is pumped past tube 72A and out the second outlet 42A.

The tube 72A is preferably disposed generally at the top of the oxygenator housing 34A and generally adjacent the outlet 42A so that one end of the tube 72A is connected to the oxygenating gas outlet 38A and the other end of the tube 72A comprises an oxygenating gas outlet for the oxygenator 12A.

The blood pressure at the flexible portion 75A of the tube 72A is communicated to oxygenating gas exiting through outlet 38A. This pressure deforms or otherwise moves the flexible portion 75A to pressurize the oxygenating gas exiting outlet 38A.

Assuming a negligible head height difference between the outlet 42A and the location of the flexible portion 75A, the pressure communicated to the oxygenating gas exiting outlet 38A will closely approximate that present in the blood flow paths of the oxygenator. More particularly, the pressure communicated to the oxygenating gas exiting outlet 38A will closely approximate that of the blood exiting the oxygenator 12A through outlet 42A.

As stated above, the pressure communicated to the flexible portion 75A may be as low as 50 mmHg to over 400 mmHg depending on the arrangement of the circuit, blood temperature, blood hematocrit, and the blood flow rate. This pressure tends to urge the flexible portion 75A of the tube 72A to close against the pressure of the oxygenating gas exiting the outlet 38A. This urging, in turn, raises the pressure of the oxygenating gas exiting the first outlet 38A to approximately that of the blood in the blood flow paths. Assuming a negligible pressure drop across the oxygenator 12A, this raises the pressure of oxygenating gas within the oxygenator 12A to near yet below the blood pressure at the blood outlet 42A, which is near yet below the total blood pressure opposite the bundle 56A of the oxygenator 12A generally throughout the bundle 56A. Whatever pressure drops that do exist between the blood outlet 42A and the inlets to the fibers in the bundle 30A will only greater ensure that the pressure of the oxygenator gas at each place within the bundle 56A is below the total pressure of the blood opposite the bundle 56A generally throughout the bundle 56A.

The pressure of the oxygenating gas is self-regulating to stay near yet below the blood pressure due to the construction, location and operation of the tube 72A. In operation, there is a positive pressure at outlet 42A due to the blood flow provided by the blood pump and the resistance of the rest of the system. Typically this pressure may range from 100 to 500 mmHg above ambient depending upon the selection and size of the individual items of the extracorporeal life support system, the vascular state of the patient, and the blood flow rate. It is known that the transfer rate of a gas into a liquid such as blood is a function of the partial pressure driving force between the gas and the liquid and not the liquid pressure itself. Hence, as the blood flow increases, normally indicating increased patient oxygen demand, the oxygen transfer will be automatically increased as the higher flow is reflected as a higher pressure to the gas path by means of the flexible portion 75A of the tubing 72A. As the blood flow decreases, the opposite happens.

Again, carbon dioxide transfer may actually be impaired by the action of this invention, since the partial pressure of the carbon dioxide in the gas path will also be increased by the action of increasing the gas path pressure. However, see the discussion of membrane oxygenators above.

Generally, the user will attempt to keep the blood circuit pressure as low as possible, but optionally, the user could increase the blood pressure slightly by partially restricting the arterial line with an occluder (e.g. a Harvard clamp or the like) to obtain the increased efficiency effect in an emergency where blood flow was otherwise restricted due to cannulation, patient state, etc.

The effect of raising the gas partial pressure within the oxygenator 12A is to increase the performance or efficiency of the oxygenator 12A. In addition, this effect is relative to the blood flow rate. Thus when the flow rate of blood is high and the oxygenator demands are highest, the pressure effect is also at its highest. The effect of the means 70 is that it tends to maintain performance when the performance of the oxygenator 12A is otherwise expected to diminish.

Table I demonstrates the effect of the means 70 for a typical circuit. Table 1 was generated from a computer model.

| Blood Flow Rate 1 pm (liters per minute) | Outlet 42A; Blood Pressure (mmHg) | Gas Path Pressure; generally at 38A; (mmHg) | Arterial Blood Oxygen Partial Pressure; Means 70A off; (mmHg) | Arterial Blood Oxygen Partial Pressure; Means 70A on; (mmHg) |
|---|---|---|---|---|
| 1 | 127 | 102 | 305 | 394 |
| 2 | 152 | 127 | 251 | 356 |
| 3 | 184 | 159 | 220 | 347 |
| 4 | 224 | 199 | 198 | 353 |
| 5 | 271 | 246 | 182 | 369 |
| 6 | 326 | 300 | 169 | 391 |
| 7 | 388 | 300 | 159 | 377 |

OXYGENATOR EFFECTIVENESS
45% inlet saturation, 8 gm % hemoglobin, 100% fiO2, 37° C.

Optionally, as in the computer model, the oxygenating gas pressure at the outlet 38A may be limited to some predetermined amount such as 300 mmHg, by any suitable pressure limiting means such as, but not limited to, a non heat sealed collapsible element connected to the wall of cap 62A. Note the data for flow rates of six and seven liters per minute. This further reduces the chances of a gas embolism.

A prototype oxygenator 12A was constructed by modifying a SARNS ™ 9443 Adult membrane Oxygenator generally available from Sarns of Ann Arbor, Mich. The oxygenator 12A was modified as shown in FIG. 8 and included the tube 72A with a resilient portion 75A. Additionally, portions of the gas flow path were closed off by sealing both of the ends of some of the fibers in the bundle 56A. The fibers were sealed to test the increased efficiency of the means 70A. The modified oxygenator was tested at four (4) liters per minute with various back pressures in the blood.

One advantage of the oxygenator 12A is that it may be conveniently constructed using a method comprising the steps of: (1) providing a housing 34A having a hollow portion, (2) providing a plurality of hollow fibers in a bundle 56A having a pair of opposite ends, (3) providing a tube 72A having a flexible resilient portion 75A and a relatively rigid portion 76A and a pair of opposite ends, (4) placing the tube 72A and the bundle 56A in the hollow portion of the housing 34A, (5) sealing the tube 72A and the bundle 56A within the hollow portion of the housing 34A with a sealant compound, and (6) then generally simultaneously cutting the ends of bundle 56A and the tube 72A to provide oxygenating gas flow paths through the hollow fibers and the tube 72A.

The above described method allows the means 70 to be created at the same time and by the same method as the rest of the oxygenator 12A including the bundle 58A. This allows cost, safety, response, and reliability improvements.

From the foregoing, it will be apparent that various modifications and changes may be made by those skilled in the art without departing from the spirit and scope of the invention described herein. Because these modifications and changes may be made by one skilled in the art and without departing from the scope and spirit of the invention, all matters shown and described are to be interpreted as illustrative and not in a limiting sense.

I claim:

1. A membrane oxygenator comprising:

a housing having means defining a hollow portion, transfer membrane means comprising a hollow fiber bundle disposed within the hollow portion of the housing and defining oxygenating gas flow paths between an oxygenating gas inlet and an oxygenating gas outlet and through individual fibers in said hollow fiber bundle, and defining blood flow paths between a blood inlet and a blood outlet, said blood flow paths being around individual fibers in said hollow fiber bundle; and automatic maintaining means for automatically maintaining the total pressure of the oxygenating gas at each point within the gas flow paths sufficiently near yet below the total pressure of the blood opposite the transfer membrane means generally throughout the oxygenator to avoid bubbling the oxygenating gas into the blood, said automatic maintaining means comprising tube having a flexible portion within said housing, said flexible portion being adapted to restrict the flow of oxygenating gas exiting through said oxygenating gas outlet by being deflected by a pressurization fluid at approximately the pressure of the blood exiting through said blood outlet to thereby raise the pressure of the oxygenating gas within the oxygenator near that of the exiting blood, wherein the pressurization fluid comprises blood, and wherein the pressurization fluid and oxygenating gas outlet are situated in the hollow portion of the housing.

2. A membrane oxygenator comprising:

a housing having means defining a hollow portion, transfer membrane means comprising a hollow fiber bundle disposed within the hollow portion of the housing and defining oxygenating gas flow paths between an oxygenating gas inlet and an oxygenating gas outlet and through individual fibers in said hollow fiber bundle, and defining blood flow paths between a blood inlet and a blood outlet, said blood flow paths being around individual fibers in said hollow fiber bundle; and automatic maintaining means for automatically maintaining the total pressure of the oxygenating gas at each point within the gas flow paths sufficiently near yet below the total pressure of the blood opposite the transfer membrane means generally throughout the oxygenator to avoid bubbling the oxygenating gas into the blood, said automatic maintaining means being at least partially located within said housing and comprising means for restricting the flow of oxygenating gas exiting through said oxygenating gas outlet with approximately the pressure of blood exiting through said blood outlet by providing a pressurization fluid with approximately the pressure of the blood exiting through said blood outlet to raise the pressure of the oxygenating gas within the oxygenator near that of the exiting blood, wherein the oxygenating gas outlet is situated within the hollow portion of the housing.

3. An oxygenator according to claim 2 wherein said automatic maintaining means comprises a tube situated within the hollow portion of the housing, said tube having an inlet connected to the oxygenating gas outlet and an oxygenator outlet for passage of the oxygenating gas out of the oxygenator, and said tube has a flexible resilient portion adapted to be partially collapsed by said pressurization fluid and a relatively rigid portion adapted to resist collapse due to said pressurization fluid.

4. An oxygenator according to claim 3 wherein said flexible, resilient portion is situated generally adjacent said blood outlet.

5. A membrane oxygenator comprising:

a housing having a hollow portion, transfer membrane means comprising a hollow fiber bundle disposed within the hollow portion of the housing and defining oxygenating gas flow paths between an oxygenating gas inlet and an oxygenating gas outlet and through individual fibers in said hollow fiber bundle, and defining blood flow paths between a blood inlet and a blood outlet, said blood flow paths being around individual fibers in said hollow fiber bundle; and maintaining means for maintaining the total pressure of the oxygenating gas at each point within the gas flow paths sufficiently near yet below the total pressure of the blood opposite the transfer membrane means generally throughout the oxygenator to avoid bubbling the oxygenating gas into the blood, said maintaining means comprising means for restricting the flow of oxygenating gas exiting through said oxygenating gas outlet by providing a pressurization fluid with approximately the pressure of the blood in the blood flow paths to raise the pressure of the oxygenating gas within the oxygenator to increase the efficiency of the oxygenator, wherein the pressurization fluid and oxygenating gas outlet are situated in the hollow portion of the housing.

6. An oxygenator according to claim 5 wherein the pressurization fluid comprises blood.

7. A membrane oxygenator comprising:

a housing having a hollow portion, transfer membrane means comprising a hollow fiber bundle disposed within the hollow portion of the housing and defining oxygenating gas flow paths between an oxygenating gas inlet and an oxygenating gas outlet and through individual fibers in said hollow fiber bundle, and defining blood flow paths between a blood inlet and a blood outlet, said blood flow paths being around individual fibers in said hollow fiber bundle; and maintaining means for maintaining the total pressure of the oxygenating gas at each point within the gas flow paths sufficiently near yet below the total pressure of the blood opposite the transfer membrane means generally throughout the oxygenator to avoid bubbling the oxygenating gas into the blood, said maintaining means comprising a tube with a flexible portion located within the housing that restricts the flow of oxygenating gas exiting through the oxygenating gas outlet by being deflected by a pressurization fluid with approximately the pressure of the blood in the blood flow paths to raise the pressure of the oxygenating gas within the oxygenator to increase the efficiency of the oxygenator wherein the oxygenating gas outlet is situated within the hollow portion of the housing.

8. An oxygenator according to claim 7 wherein said maintaining means comprises a tube situated within the hollow portion of the housing, said tube having an inlet connected to the oxygenating gas outlet and an oxygenator outlet for passage of the oxygenating gas out of the oxygenator, and said tube has a flexible resilient portion adapted to be partially collapsed by said pressurization fluid and a relatively rigid portion for resisting collapse due to said pressurization fluid.

9. An oxygenator according to claim 8 wherein said flexible, resilient portion is situated generally adjacent said blood outlet.

10. An oxygenator according to claim 7 wherein the pressurization fluid is approximately the pressure of blood exiting the oxygenator through said blood outlet.

11. An oxygenator according to claim 8 wherein said tube has a means for preventing complete occlusion of the oxygenating gas flow.

* * * * *

UNITED STATES PATENT AND TRADEMARK OFFICE
CERTIFICATE OF CORRECTION

PATENT NO. : 5,382,407
DATED : January 17, 1995
INVENTOR(S) : Ronald J. Leonard

It is certified that error appears in the above-indentified patent and that said Letters Patent is hereby corrected as shown below:

On the cover page, under "Related U.S. Application Data", line 3, "248,092" should be --284,092--.

Col. 6, line 54, after "size" insert --of--.

Col. 14, line 30, after "comprising" insert --a--.

Signed and Sealed this

Eighteenth Day of July, 1995

Attest:

BRUCE LEHMAN

*Attesting Officer*  *Commissioner of Patents and Trademarks*